United States Patent [19]

Mulder

[11] Patent Number: 5,578,317
[45] Date of Patent: Nov. 26, 1996

[54] WOUND FILLER AND METHOD OF MANUFACTURE

[76] Inventor: Gerit D. Mulder, 4850 S. Lafayette La., Englewood, Colo. 80110

[21] Appl. No.: 415,177

[22] Filed: Mar. 31, 1995

[51] Int. Cl.$^6$ .................................................. A61F 13/00
[52] U.S. Cl. ............................................ 424/443; 424/445
[58] Field of Search ..................................... 424/443, 445

[56] References Cited

U.S. PATENT DOCUMENTS

| | | | |
|---|---|---|---|
| 4,767,463 | 8/1988 | Brode et al. | 106/162 |
| 5,064,653 | 11/1991 | Sessions et al. | 424/445 |
| 5,089,606 | 2/1992 | Cole et al. | 536/54 |
| 5,110,593 | 5/1992 | Benford | 424/401 |
| 5,154,928 | 10/1992 | Andrews | 424/445 |
| 5,227,168 | 7/1993 | Chvapil et al. | 421/445 |
| 5,238,685 | 8/1993 | Wren | 424/445 |
| 5,264,218 | 11/1993 | Rogozinski | 424/445 |
| 5,298,015 | 3/1994 | Komatsuzaki et al. | 602/46 |

*Primary Examiner*—Paul R. Michl
*Assistant Examiner*—Sharon Howard
*Attorney, Agent, or Firm*—Duft, Graziano & Forest, P.C.

[57] ABSTRACT

A wound filler or dressing includes a sterile polyurethane foam pad having cell openings that are impregnated with an antimicrobial odor-reducing agent. The antimicrobial odor-reducing agent is preferably 8-hydroxyquinoline, which may be mixed with a liquid carrier for introduction to cell openings of the pad. The antimicrobial odor-reducing agent inhibits the production of microbial odors from wound exudate that is absorbed by the pad.

10 Claims, 2 Drawing Sheets

WOUND FILLER AND METHOD OF MANUFACTURE

BACKGROUND OF THE INVENTION

1. Field of the Invention

The present invention pertains to the field of wound care dressings and, more particularly, to wound filler products that are used for the treatment of penetrating wounds to the skin, as well as methods of making such products. Still more specifically, the wound filler or dressing includes a flexible polymer foam that is impregnated with an antimicrobial or odor-reducing agent.

2. Description of the Prior Art

Current injury treatment modalities consist of applications of various types of foams, gauze, adhesive synthetic dressings, and antimicrobial ointments. Conventional wound filler products include foam dressings that are applied over large penetrating wounds to the skin and underlying tissues. The foams are flexible and compressibly conform with areas proximal to the wound.

Commercially available polyurethane foams can be used for this purpose. A problem exists because bacteria will grow in exudate that the foam absorbs from the wound. Bacteria grow in the exudate and create unpleasant odors as well as a risk of infecting the wound site if the dressing is not timely changed. The constant need for dressing changeover is a source of pain, discomfort and anxiety to the patient. Another problem with these foams is the fact that they compress to a flattened structure over the wound site without filling the interior wound. The flattened structure permits exudate to accumulate in the wound and wound damage can occur.

U.S. Pat. No. 5,110,593, issued to Benford, describes a topical ointment for use in treating diaper dermatitis. An antimicrobial or odor-reducing agent consisting of 0.22% 8-hydroxyquinoline is combined with other ingredients The 8-hydroxyquinoline is recognized in the art as an antimicrobial or odor-reducing agent.

There remains a need for a non-irritating wound filler product that requires less frequent changeover, produces fewer unpleasant odors, and can expand into the wound site.

SUMMARY OF THE INVENTION

The present invention overcomes the above-identified problems by providing a wound filler product that requires less frequent changeover than conventional wound filler products, reduces the incidence of unpleasant odors, and expands into the wound site for sealing action.

The wound filler includes a flexible foam member having a matrix defining a plurality of interconnected cell openings that are impregnated with an antimicrobial or odor-reducing agent. The cell openings have small openings that enable them to imbibe wound exudate. The antimicrobial or odor-reducing agent is present in an effective amount for inhibiting the production of microbial odors in wound exudate that is absorbed in the openings.

In preferred embodiments, the antimicrobial or odor-reducing agent is 8-hydroxyquinoline, and the effective amount preferably ranges up to about 5% of the total weight of the foam member and the odor-reducing agent. This effective amount more preferably ranges from 0.2% to 2% by weight, and even more preferably ranges from 0.9% to 1% by weight. The most preferred 8-hydroxyquinoline weight is 0.95%. The foam member is preferably a hydrophilic polyurethane foam having a porosity ranging from 40% to 90%, or an average cell diameter of 0.005 inches to 0.020 inches. This foam member preferably has a cylindrical shape, and expands when contacted with liquid. An adhesive strip may be attached to the foam member for use in retaining the foam member in a fixed position on the skin proximal to an injury site.

The wound filler product is manufactured according to a general method. A hydrophilic polyurethane foam member is provided having a matrix defining a plurality of cell openings therein. An antimicrobial odor-reducing agent portion is mixed with a liquid carrier portion to form a mixture, which is introduced to the cell openings. The carrier portion is evaporated or removed to leave a residue including the antimicrobial odor-reducing agent in an effective amount for inhibiting the production of microbial odors from wound exudate that may enter the foam cells. Again, the antimicrobial odor-reducing agent is preferably 8-hydroxyquinoline. Acetone and water are preferably mixed in a 1:2 ratio as the liquid carrier portion. The removal step preferably includes compressing the foam to remove excess amounts of the mixture and drying the foam in a convection oven at a temperature less than about 100° F.

DETAILED DESCRIPTION OF THE PREFERRED EMBODIMENT

Figure 1:
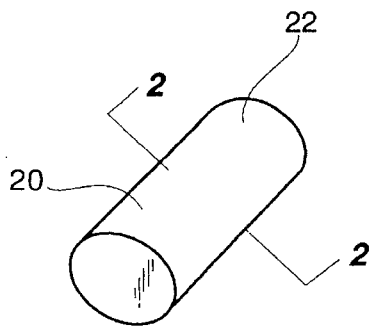
FIG. 1 depicts a wound filler dressing according to the present invention.

FIG. 1 depicts a cylindrical pad 20 that is made of a flexible hydrophilic polyurethane foam. Pad 20 presents a water and air permeable outer surface 22 for compression against an injury site. The foam material is commercially available and may be purchased, for example, as formulation No. HPF-L00562 from Rynel Ltd, Inc., of Boothby, Me. The Rynel foam is particularly preferred for its ability to expand up to 100%, 200% or more when contacted with water. The commercial varieties of these foams are not impregnated with an antimicrobial odor-reducing agent, and typically have porosities ranging from 25% to 90%.

Generally, flexible polyurethane foams are based on polyoxypropylenediols of 2000 molecular weight and triols up to 4000 molecular weight. Preferred foams have total porosities (i.e., interstitial volumes) ranging from 70% to 90%, with 85% being most preferred. Pad 20 may also be provided in less preferred geometries, such as square or rectangular pads. A preferred square pad has dimensions including a depth and width ranging from three to eight inches and a thickness of one to three inches. A preferred cylindrical pad 20 has dimensions of from four inches to one foot in length and a diameter of from two to four inches.

Figure 2:
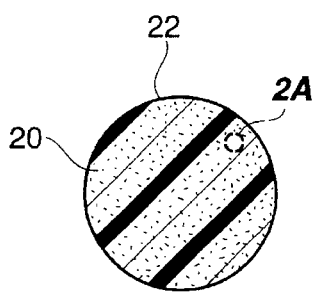
FIG. 2 depicts a sectional view of the wound filler dressing of FIG. 1 taken along line 2'—2' thereof, a magnified section shows a porous structure impregnated with an antimicrobial odor-reducing agent.
Figure 2A:
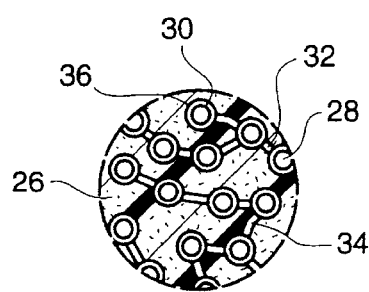

FIG. 2 depicts a sectional view taken along line 2'–2' of FIG. 1, and also presents a magnified bubble "A". Bubble A schematically illustrates a greatly magnified portion of the sectional view, and shows the porous structure of pad 20. Pad 20 contains a flexible polymer matrix 26 (e.g., polyurethane) that defines a plurality of cells, e.g., spherical cells 28 and 30, which are interconnected by capillary passageways such as passageways 32 and 34. The cells and passageways absorb or imbibe wound exudate that may be presented at surface 22. The exudate absorption is assisted by the surface tension of the exudate, which moves into the pad by capillary action and surface adhesion forces. Cells 28 and 30 as well as passageways 32 and 34 are lined with a coating of a solid antimicrobial odor-reducing agent, e.g., coating 36 of cell 30.

It should be understood that FIG. 2 is merely intended to illustrate a generic polymer foam. The geometries and scale of cells 28 and 30, as well as passageways 32 and 34, may vary considerably between different types of polymer foam. For example, matrix 26 may form irregular juxtaposed shaped sheets that interconnect cell openings 28 and 30. Capillary passageways 32 and 34 may be nonexistent. Generally, cells 28 and 30 together with passageways 32 and 34 provide a total porosity or percentage of interstitial space within pad 20. This total porosity is sometimes different from an effective porosity, which is hereby defined as a portion of the total (dry state) porosity that is capable of imbibing wound exudate or other fluids. The effective porosity can be any value equal to or less than the total porosity. Porosity is difficult to measure in the preferred polyurethane foams because they expand with imbibition of liquid. Average cell sizes are often used as an indicator of porosity, and these typically range from 0.005 to 0.0–20 inches in diameter for spherical cells in the preferred foams.

Antimicrobial odor-reducing agent 36 is present in an effective amount for inhibiting odors caused by microbial growth in wound exudate that is absorbed into pad 20. The most preferred antimicrobial odor-reducing agent is 8-hydroxyquinoline, though, other known odor-reducing agents or biocides may be used in approved concentrations. Commercial sources of 8-hydroxyquinoline include, for example, Fisher Pharmaceutical, which lists 8-hydroxyquinoline as product number 0261-100. The 8-hydroxyquinoline is most preferred for its low sensitizing effect on wounds. Other antimicrobial agents are more likely to induce adverse reactions in sensitive patients with long term exposure. The 8-hydroxyquinoline is preferably present in an amount ranging up to 5% of the total combined weight of 8-hydroxyquinoline and the polyurethane matrix "w/w"). This range more preferably ranges from 0.2% to 2% w/w. Even more preferably, the amount of 8-hydroxyquinoline ranges from 0.9% to 1% w/w, with the most preferred amount being 0.95%.

Figure 3:
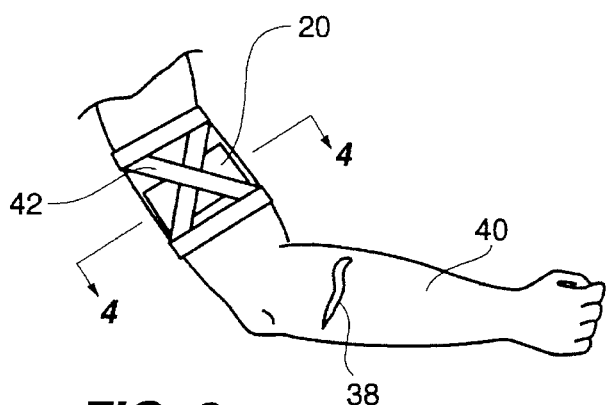
FIG. 3 depicts the wound filler dressing of FIG. 1 bound in place with an adhesive strip proximal to a wound site.

FIG. 3 depicts pad 20 retained in a fixed position over a wound site on arm 40. The would site is not depicted in FIG. because it underlies pad 20, however, the underlying wound may be considered to be just like wound 38. A covering 42 for pad 20 is formed of adhesive tape and gauze. Covering 42 is applied to surface 22 with the tape in a figure eight over arm 40 to immobilize pad 20 with respect to arm 40.

Figure 4:
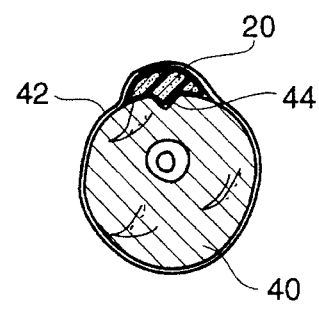
FIG. 4 depicts a sectional view of FIG. 3 taken along line 4'—4' and rotated 90° clockwise with respect to FIG. 3.

FIG. 4 depicts a sectional view taken along line 4'—4' of FIG. 3, and rotated clockwise 90° with respect to FIG. 3. Pad 20 is depicted in a compressed state that substantially fills wound 44 and contacts surrounding area. The most preferred treatment modality is to select a pad 20 of sufficient size for complete cover and fill of injury 44. The cylindrical shape, high porosity, high water absorption and flexion permit pad 20 to fill wound 44.

In use, pad 20 is positioned over wound 44 and compressed in place for a period of time. Pad 20 absorbs fluid (exudate) from wound 38 by imbibition. The absorbed fluid contacts the antimicrobial odor-reducing agent 36 for inhibition of microbial odors. Pad 20 expands slightly as it absorbs exudate to apply slightly greater compressional forces against wound 44 proximal to the area of absorption. Pad 20 may need to be periodically renewed when it becomes saturated with exudate, or when bad odors develop to indicate that the antimicrobial odor-reducing agent 36 is no longer effectively inhibiting odor production and/or microbial growth.

Figure 5:
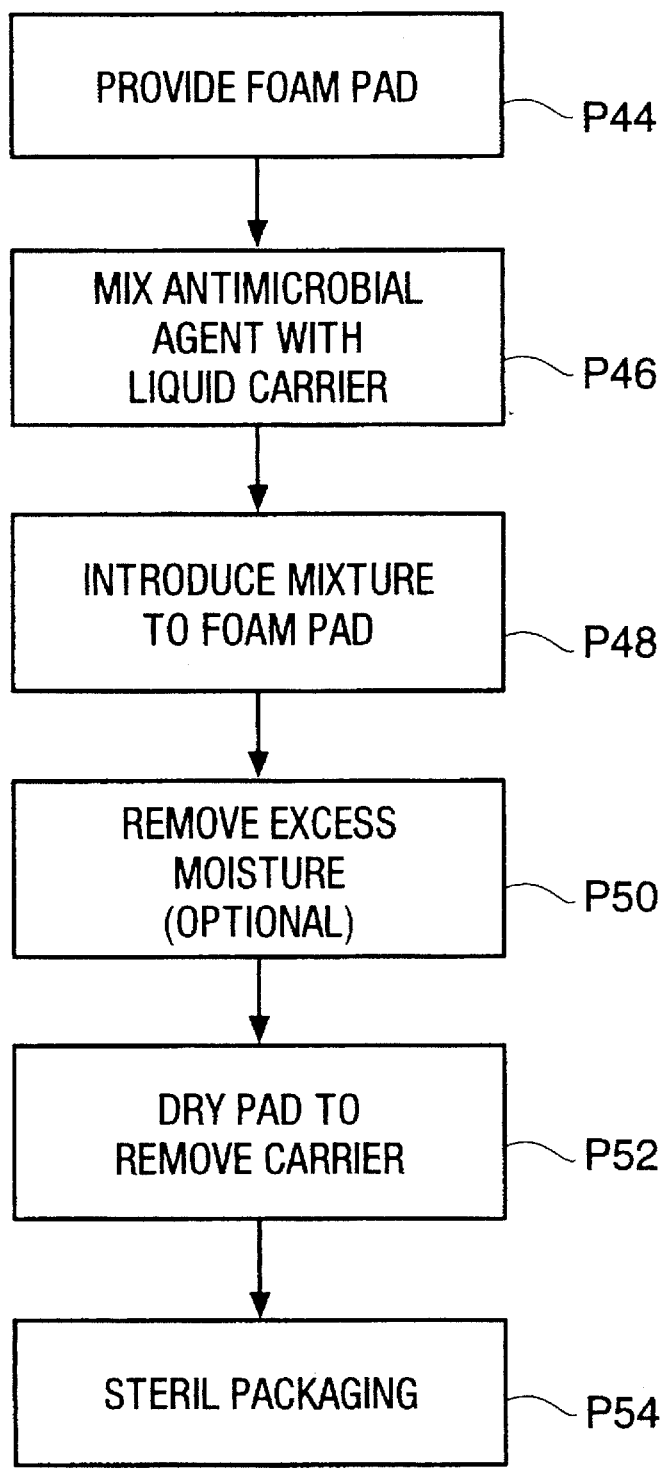
FIG. 5 depicts a process diagram for manufacturing the wound filler dressing of FIG. 1.

Pad 20 is manufactured according to the process of FIG. 5, which is preferably conducted under sterile conditions. Step P44 includes providing a sterile polyurethane foam pad, which may be acquired from commercial sources.

Step P46 includes mixing an antimicrobial odor-reducing agent with a liquid carrier. When 8-hydroxyquinoline is the antimicrobial odor-reducing agent, the liquid carrier preferably includes a mixture of acetone and water. This mixture preferably includes a ratio of acetone to water ranging from 1:1 to 3:1, with a 1:2 ratio being most preferred. The concentration of 8-hydroxyquinoline varies depending upon the porosity of pad 20 and the degree, if any, to which pad 20 will be compressed in removing excess amounts of the mixture. Pad 20 will preferably have an effective porosity (i.e., a porosity which can be reached by fluids) of from about 80% to 90% and a density of about 0.12 g/cc.

The amount of the antimicrobial odor-reducing agent to be added to solution can be determined from the following equation:

$$X = w/(w+W) \quad (1)$$

wherein w is the weight of antimicrobial odor-reducing agent in solution as grams; W is the weight of dry foam in grams, and X is the desired weight percent of 8-hydroxyquinoline. The solution volume to which the 8-hydroxyquinoline should not exceed the amount of solution that can be absorbed by the foam.

Step P48 includes introducing the antimicrobial odor-reducing agent and carrier mixture into the foam pad. This introduction is preferably performed by soaking the pad in the mixture for complete absorption of the mixture into the pad. It is preferred to mechanically manipulate the pad for purposes of providing an even internal distribution of the liquid mixture.

Step P50 is an optional step that includes compressing the pad to remove excess amounts of the mixture. The compression preferably occurs by rolling a roller across the pad in a sterile air atmosphere to flatten the pad by no more than about one-half of its uncompressed thickness. Compression advantageously offers faster drying times and more predictable results owing to less dripping during the drying step. Nevertheless, the concentration of antimicrobial odor-reducing agent will need to be increased to compensate for the loss of fluid. For example, compression of an 80% porosity foam to 60% of its initial volume will eliminate about 40% or half of the porosity, i.e., the foam will be 40% porous in the compressed state. For a given type of foam, empirical trials can easily establish appropriate standards for the concentration of 8-hydroxyquinoline, solution volume, and degree of compression, as needed to produce a given weight percent of the odor reducing agent in the foam. These trials are conducted by varying the concentration, volume, and compression factors at regular intervals, and comparing the weight of the foam both before and after the odor reducing agent is introduced to the foam.

Step P52 includes drying the pad in a convection oven for a sufficient time to remove substantially all of the carrier liquid and desiccate the antimicrobial odor-reducing agent. The most preferred drying profile occurs at a temperature of from 73° C. to 75° C. for an interval ranging from about four to twenty four hours. These temperatures approximate, but do not exceed the melting point of 8-hydroxyquinoline. The drying time should be sufficient to eliminate substantially all of the liquid carrier portion and leave a desiccated residue of the antimicrobial odor-reducing agent. The final product is preferably cooled and packaged in a sterile paper container.

Those skilled in the art will understand that the preferred embodiments described above may be subjected to apparent modifications without departing from the true scope and spirit of the invention. Accordingly, the inventor hereby states his intention to rely upon the Doctrine of Equivalents to protect his full rights in the invention.

I claim:

1. A wound dressing for use in treating penetrating wounds to skin tissue, comprising:

a flexible foam member having a matrix defining a plurality of interconnected cell openings therein, said foam member having a cylindrical shape and sufficient flexion to permit substantial filling of a wound as said foam member is compressed over said wound, said cell openings being capable of absorbing wound exudate; and an effective amount of 8-hydroxyqinoline received within said cell openings for inhibiting production of microbial odors from wound exudate absorbed in said cell openings.

2. The dressing as set forth in claim 1, said effective amount determined as a percentage of a total weight consisting of said member and said antimicrobial odor-reducing agent is 8-hydroxyquinoline.

3. The dressing as set forth in claim 2, said percentage of 8-hydroxyquinoline ranging from about 0.2% to about 2% of said total weight.

4. The dressing as set forth in claim 1, said foam member being a hydrophilic polyurethane foam capable of expanding when contacted with wound exudate.

5. The dressing as set forth in claim 4, said foam having an average cell size ranging 0.005 inches to 0.020 inches.

6. A method of making a wound dressing for use in treating penetrating wounds to skin tissue, said method comprising the steps of:

providing a cylindrical hydrophilic polyurethane foam member having a matrix defining a plurality of interconnected cell openings therein, said cell openings being capable of absorbing wound exudate;

mixing 8-hydroxyquinoline with a liquid carrier portion to form a mixture;

introducing said mixture to said cell openings; and removing said carrier to leave in said cell openings a residue including said antimicrobial odor-reducing agent in an effective amount for inhibiting production of microbial odors from wound exudate absorbed in said cell openings.

7. The method as set forth in claim 6 wherein said mixing step includes a step of combining said 8-hydroxyquinoline as said antimicrobial odor-reducing portion with acetone and water as said liquid carrier portion.

8. The method as set forth in claim 7, wherein said liquid carrier portion includes one part acetone and two parts water by volume.

9. The method as set forth in claim 6, wherein said removing step includes compressing said foam to remove excess amounts of said mixture and drying said foam in a convection oven at a temperature less than about 100° F.

10. A wound dressing produced according to the method of claim 6.

* * * * *